United States Patent [19]

Tang

[11] Patent Number: 4,517,372
[45] Date of Patent: May 14, 1985

[54] PROCESS FOR THE PREPARATION OF 4-FLUOROPHTHALIC ANHYDRIDE

[75] Inventor: David Y. Tang, E. Amherst, N.Y.

[73] Assignee: Occidental Chemical Corporation, Niagara Falls, N.Y.

[21] Appl. No.: 604,272

[22] Filed: May 2, 1984

Related U.S. Application Data

[63] Continuation-in-part of Ser. No. 493,849, May 12, 1983, abandoned.

[51] Int. Cl.³ .......................................... C07D 307/89
[52] U.S. Cl. .................................................. 549/246
[58] Field of Search ........................................ 549/246

[56] References Cited

U.S. PATENT DOCUMENTS 3,480,667  11/1969  Siegart et al. ................... 549/246
3,956,321  5/1976  Markezich ........................ 549/246

OTHER PUBLICATIONS

Bergmann, J.A.C.S., vol. 64 (1942) pp. 176 & 177.

*Primary Examiner*—Richard L. Raymond
*Attorney, Agent, or Firm*—James F. Tao; Arthur S. Cookfair

[57] ABSTRACT

This invention relates to a process for the preparation of 4-fluorophthalic anhydride which comprises contacting a dihalohexahydrophthalic anhydride of the formula

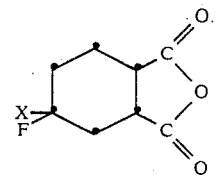

where X is Cl or F, with a dehydrogenation catalyst. Advantageously, the process of the invention may be carried out in the presence of a hydrogen acceptor. The preferred hydrogen acceptor is a halocarbon hydrogen acceptor of the formula

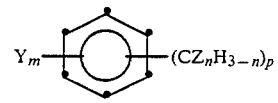

where Y is Cl, Br, or I; Z is Cl, Br or I; m is 0 to 4, n is 0 to 3, p is 0 to 3, and m+n is at least 1; with the proviso that when m is 0, p is at least 1.

20 Claims, No Drawings

PROCESS FOR THE PREPARATION OF 4-FLUOROPHTHALIC ANHYDRIDE

BACKGROUND OF THE INVENTION AND INFORMATION DISCLOSURE STATEMENT

This application is a continuation-in-part of application Ser. No. 493,849, for "Process for the Preparation 4-Fluorophthalic Anhydride", filed May 12, 1983, now abandoned.

This invention relates to a method for the preparation of 4-fluorophthalic anhydride by contacting 4,4-difluorohexahydrophthalic anhydride or 4-chloro-4-fluorohexahydrophthalic anhydride with a dehydrogenation catalyst. The compound prepared is disclosed in the literature to be useful in the preparation of aromatic ether and thioether anhydride curing agents, antioxidants and polyetherimide polymers. Examples of the utility of 4-fluorophthalic anhydride and the various prior art methods for the synthesis thereof are disclosed in U.S. Pat. Nos. 3,850,965 and 3,956,321.

The preparation of tetrahydrophthalic anhydrides and aromatization thereof dehydrogenation under various conditions is known in the chemical literature. Skvarchenko et al., Obshchei Khimii, Vol. 30, No. 11, pp. 3535–3541 disclose the aromatization of chloro-substituted tetrahydrophthalic anhydride by heating with phosphorus pentoxide. In the aromatization process described, however, decarboxylation also occurs with the formation of the corresponding chloro-substituted benzene compound. The preparation of tetrahydrophthalic acids and anhydrides and various methods for dehydrogenation and aromatization thereof are reviewed by Skvarchenko in Russian Chemical Review, No. 1963, pp. 571–589.

Bergmann, J. Amer. Chem. Soc., 64, 176 (1942) discloses the aromatization of tetrahydrophthalic anhydride products of Diels-Alder reactions. The author discloses that dehydrogenation occurred when the tetrahydrophthalic anhydride product was boiled in nitrobenzene. However, it was further disclosed that dehydrogenation did not occur when p-bromonitrobenzene, p-chloronitrobenzene, or m-dinitrobenzene in xylene was employed.

The following U.S. Patents provide further background relative to the chemistry of cyclic anhydrides and halo-substituted cyclic anhydrides: U.S. Pat. Nos. 1,891,843 to Shaw et al; 2,391,226 to Clifford et al.; 2,764,597 to Barney, 3,240,792 to Patrick et al.; 3,346,597 to Acetis; 3,480,667 to Siegart et al.; 3,819,658 to Gormley et al.; 4,045,408 to Griffith et al.; and 4,302,396 to Tsujimoto et al.

SUMMARY OF THE INVENTION

It has now been found that 4-fluorophthalic anhydride can be prepared by contacting a dihalohexahydrophthalic anhydride of the formula

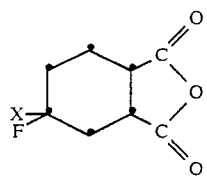

where X is Cl or F with a dehydrogenation catalyst. Optionally, the dehydrogenation reaction is carried out in the presence of a hydrogen acceptor. The preferred hydrogen acceptor is a halocarbon hydrogen acceptor of the formula

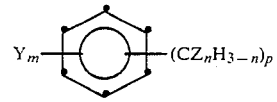

where Y is Cl, Br or I; Z is Cl, Br or I; m is 0 to 4; n is 0 to 3, p is 0 to 3, and m+n is at least 1; with the proviso that when m is 0, p is at least 1.

DETAILED DESCRIPTION

As indicated above, the present invention relates to a process for preparing 4-fluorophthalic anhydride which comprises contacting a dihalohexahydrophthalic anhydride with a dehydrogenation catalyst. Advantageously, the process of the present invention is carried out in the presence of a hydrogen acceptor.

The starting materials for the process of the invention are 4-chloro-4-fluoro-hexahydrophthalic anhydride or, preferably, 4,4-difluorohexahydrophthalic anhydride. Those compounds are conveniently prepared by reaction of hydrogen fluoride with a 4-chlorotetrahydrophthalic anhydride as illustrated by the following equation.

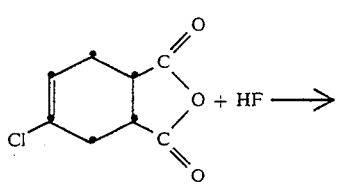

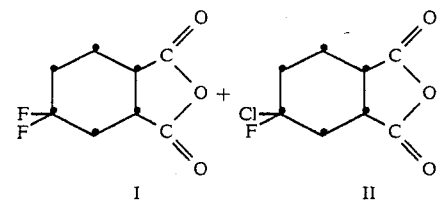

Detailed description of the methods of synthesizing these starting materials for the process of this invention is disclosed in the commonly assigned application of Cotter et al, Ser. No. 604,271, entitled "4,4-Dihalohexahydrophthalic Anhydride" and concurrently filed herewith. Said Cotter et al application is a continuation-in-part of application Ser. No. 493,856, filed May 12, 1983 now abandoned.

Based on the nomenclatural system currently utilized by Chemical Abstracts, the compounds represented by formulas I and II above, are named, respectively, 5,5-difluoro-3a,4,5,6,7,7a-hexahydro-1,3-isobenzofurandione, and 5-chloro-5-fluoro-3a,4,5,6,7,7a-hexahydro-1,3-isobenzofurandione. For convenience, these compounds will be referred to hereinafter by names derived from common nomenclature, that is, 4,4-difluorohexahydrophthalic anhydride and 4-chloro-4-fluoro-hexahydrophthalic anhydride, respectively.

Dehydrogenation catalysts suitable for the process of this invention include the platinum, palladium, rhodium, ruthenium, rhenium, iridium or nickel metals, either in elemental form or as an M° compound or complex thereof, either unsupported or on a suitable support. Other suitable catalyst include copper chromite, which is believed to have the formula $CuO \cdot Cr_2O_3$, chromium oxide, molybdenum oxide, tungsten oxide, and vanadium oxide. Typical catalyst supports include for example activated carbon, charcoal, silicon carbide, silica gel, alumina, acidic silica-alumina, silica, titania, zirconia, kieselguhr, mixed rare earth oxides, carbonates, barium carbonate, barium sulfate, calcium carbonate, pumice, silica alumina mixtures, zeolites, and the like. Suitable catalytic complexes include the M° compounds where M is Pd, Pt, Ni, rhodium or ruthenium, and is bound in the structure by phosphine, phosphite or carbamyl ligands. Complexes of this type are generally soluble in the reaction mixtures employed in the process of this invention. Typical complexes include: tetrakis(triphenylphosphine)platium (O); Bis[bis(1,2-diphenylphosphino)ethane]palladium (O); Bis[bis(1,2-diphenylphosphino)benezene]palladium (O); Bis(1,5-cyclooctadiene)nickel (O); Tetrakis(triethylphosphite)-nickel (O); Tetrakis(triphenylphosphine)nickel (O) and tetrakis(triphenylphosphite)nickel (O); chlorotris(triphenylphosphine) rhodium (I); and dichlorotris(triphenylphosphine) ruthenium (II).

As indicated above, the process of the present invention may be advantageously carried out in the presence of a hydrogen acceptor. The hydrogen acceptors which may be employed in the process of this invention include those materials known in the art as hydrogen acceptors in like reactions. For example, the hydrogen acceptors include olefins containing 2 to 20 carbon atoms, aromatic nitro-compounds such as nitrobenzene, certain carbonyl compounds such as aldehydes and ketones, and certain halocarbon compounds capable of exchanging at least one chlorine, bromine, or iodine atom per molecule for a hydrogen atom.

The halocarbon hydrogen acceptors suitable for use in the process of the invention include chloro-, bromo-, and iodoaromatic wherein the chloro-, bromo-, or iodo-, substituent is present either on the aromatic ring or on a side-chain such as an alkyl or alkoxy side-chain. Haloaromatics suitable for this purpose include, for example, halobenzenes such as chlorobenzene, dichlorobenzene, trichlorobenzene, tetrachlorobenzene, bromobenzene, dibromobenzene, tribromobenzene, tetrabromobenzene; halotoluenes such as orthochlorotoluenes, orthobromotoluenes, dibromotoluene, tribromotoluene, tetrabromotoluene orthoiodotoluene, metaiodotoluene, paraiodotoluene, diiodotoluenes, triiodotoluenes, tetraiodotoluenes; benzylchlorides, such as 2-chlorobenzyl chloride, 2,6-dichlorobenzylchloride, 2,3,6-trichlorobenzylchloride; benzalchlorides, benzotrichloride, benzylbromide, benzalbromide, benzotribromide, benzyliodide, orthochlorobenzotrichloride, parachlorobenzotrichloride, parachlorobenzotrifluoride, various halogenated fused ring aromatics, such as the halonaphthalenes and haloanthracenes, wherein the halo is chloro, bromo or iodo.

The process may be run either in the liquid phase or in the vapor phase. If an insoluble catalyst is employed, it is preferred to utilize the catalyst in finely divided form, with agitation or stirring to maintain the catalyst in dispersed form throughout the reaction medium. The process is preferably run at a temperature of between about 150° to 400°, and most preferably about 250° to about 350° Celsius. The process may be run at either atmospheric, subatmospheric or superatmospheric conditions. If the operating temperature is below the boiling point of the reaction mixture, the reaction may be run conveniently at atmospheric pressure. However if an operating temperature is selected above the boiling point of the reaction mixture it is preferred to utilize a sealed reactor or autoclave and operate at autogenous pressures. When the reaction is to be carried out in the vapor phase, and if the vaporization temperature of some of the materials in the reaction is high enough to be possibly deleterious to other materials in the reaction, then the reaction may be advantageously carried out at reduced pressures or subatmospheric conditions.

The following specific examples are provided to further illustrate this invention and the manner in which it may be carried out. It will be understood, however, that the specific details given in the examples have been chosen for purpose of illustration and are not to be construed as limitations on the invention. In the examples, unless otherwise indicated, all parts and percentages are by weight and all temperatures are in degrees Celsius.

EXAMPLE 1

A mixture of 50.0 parts of 4,4-difluorohexahydrophthalic anhydride and 10 parts of 5 percent palladium of carbon (Pd/C) catalyst in 578 parts of 1,2,4-trichlorobenzene was heated to reflux conditions and maintained at reflux for about 16 hours, with stirring. The reaction mixture was then cooled to about room temperature. Analysis of the reaction product using gas chromatographic techniques, indicated a yield of about 25 percent of 4-fluorophthalic anhydride, based on the difluorohexahydrophthalic anhydride reactant.

EXAMPLE 2

A mixture of 500 parts of 4,4-difluorohexahydrophthalic anhydride and 100 parts of 5 percent Pd/C catalyst in 3615 parts of 1,2,4-trichlorobenzene was charged to an autoclave reactor. The autoclave atmosphere was purged with nitrogen. The autoclave was then sealed, heated to about 250°–285° C. and maintained thereat for about 3.5 hours, then cooled to about room temperature. Analysis of the reaction product by gas chromatographic techniques, indicated a yield of about 51 percent 4-fluorophthalic anhydride, based on the difluorohexahydrophthalic anhydride reactant.

EXAMPLE 3

A mixture of 500 parts of 4,4-difluorohexahydrophthalic anhydride and 100 parts of 5 percent Pd/C catalyst in 3787 parts of o-chlorotoluene was charged to an autoclave reactor. The autoclave atmosphere was purged with nitrogen. The autoclave when then sealed, heated to 300°–350° and maintained thereat for about 3 hours, then cooled to about room temperature. Analysis of the reaction product, by gas chromatographic techniques indicated a 37 percent yield of 4-fluorophthalic anhydride, based on the difluorohexahydrophthalic anhydride reactant.

EXAMPLE 4

A mixture of 600 parts of 4,4-difluorohexahydrophthalic anhydride and 120 parts of 5 percent Pd/C catalyst in 2130 parts of 1,2,4-trichlorobenzene was charged to an autoclave reactor. The autoclave atmosphere was purged with nitrogen. The autoclave was then sealed, heated to 270°–305° and maintained thereat for about 14 hours, during which time the pressure was allowed to build gradually and was released intermittently to lower the pressure to about 115 pounds per square inch (gage), then cooled to about room temperature. Analysis of the reaction product, by gas chromatographic techniques indicated a 80 percent yield of 4-fluorophthalic anhydride, based on the difluorohexahydrophthalic anhydride reactant.

EXAMPLE 5

The procedure of Example 4 was repeated except that a mixture of 40 parts of 4,4-difluorohexahydrophthalic anhydride, 68 parts of 2-chlorobenzyl chloride and 2 parts of 5% Pd/c catalyst was used. The mixture was heated in an autoclave to 285°–305° C. for 7 hours with constant release of pressure. Analysis of the reaction product by gas chromatography mass spectrum indicated 4-fluorophthalic anhydride to be the major product.

EXAMPLE 6

The procedure of Example 4 was repeated except that a mixture of 104 parts of 4,4-difluorohexahydrophthalic anhydride, 407 parts of 2,6-dichlorobenzyl chloride and 11 parts of 5% Pd/c catalyst was used. The reaction was carried out in an autoclave at 265°–275° for 15 hours with constant release of the pressure. The product mixture was analyzed by gas chromatography-mass spectrum and 4-fluorophthalic anhydride was found to be the major product.

EXAMPLE 7

For purposes of comparison, a mixture of 500 parts of 4,4-difluorohexahydrophthalic anhydride and 100 parts of 5 percent Pd/C catalyst in 2165 parts of toluene was charged to an autoclave reactor. The autoclave atmosphere was purged with nitrogen. The autoclave was then sealed, heated to about 250°–280° C. and maintained thereat for about 5 hours, then cooled to about room temperature. Analysis of the reaction product by gas chromatographic techniques, indicated a yield of only about 2.7 percent 4-fluorophthalic anhydride, based on the difluorohexahydrophthalic anhydride reactant.

EXAMPLE 8

For purposes of comparison, a mixture of 500 parts of 4,4-difluorohexahydrophthalic anhydride and 30 parts of 5 percent Pd/C catalyst in 3000 parts of nitrobenzene was refluxed at 210° C. under a nitrogen atmosphere for about 11 hours. A sample of the reaction product was analyzed by gas chromatographic techniques. It was found that, based on the 4,4-difluorohexahydrophthalic anhydride starting material, the reaction was about 50% complete and that the reaction product contained about 13.5 percent 4-fluorophthalic anhydride and greater than 30.0 percent of various cyclic imides.

EXAMPLE 9

The procedure of Example 8 was repeated except that the catalyst employed was a 5% platinum on carbon. The reaction product was analyzed by gas chromatographic techniques as in Example 6, and 4-fluorophthalic anhydride was found to be the major product.

EXAMPLE 10

A mixture of five parts of 4,4-difluorohexahydrophthalic anhydride, one part of 5% ruthenium on carbon catalyst, and 60 parts of nitrobenzene was charged into a round-bottomed flask. The mixture was refluxed at 210° C. under a nitrogen atmosphere for about four hours. A sample of the reaction product was analyzed by gas chromatographic techniques, and 4-fluorophthalic anhydride was found to be the major product.

EXAMPLE 11

The procedure of Example 10 was repeated except that a 5% rhodium on carbon catalyst was used. After the reaction mixture was refluxed at 210° C. for about nine hours under a nitrogen atmosphere, the reaction product was analyzed by gas chromatographic techniques. 4-Fluorophthalic anhydride was again found to be the major product.

EXAMPLE 12

Gas phase reaction was carried out in a hot-tube reactor which was packed with about 30 grams of a 2% palladium on carbon catalyst. One end of the hot-tube reactor was connected to a vaporizer and the other end connected to a receiver cooled in an ice-bath. The system was connected to a source of vacuum and the pressure in the system was reduced to about 7 to 10 mm Hg. The hot-tube reactor was maintained under temperature between 290°–300° C. A mixture made of nine parts of 4,4-difluorohexahydrophthalic anhydride and 40 parts of 1,2,4-trichlorobenzene was added into the vaporizer in a dropwise fashion. The vaporizer was heated to about 200°–240° C. and the vaporized mixture was passed into the hot-tube reactor, and the reaction product was collected in the receiver. The reaction product was analyzed by gas chromatographic techniques, and 4-fluorophthalic anhydride was found to be the major product.

EXAMPLE 13

The procedure of Example 12 was repeated except that the hot-tube reactor was maintained at a temperature of about 300°–310° C. and under a reduced pressure of about 1 mm Hg. The starting material was a mixture of two parts of 4,4-difluorohexahydrophthalic anhydride and 20 parts of N-methylpyrolidone (n-pyrol). The reaction product was analyzed and again found to contain 4-fluorophthalic anhydride as the major product.

EXAMPLE 14

The procedure of Example 12 was repeated except that the hot-tube reactor was maintained at a temperature of about 200°–250° C. under pressure of about 0.5 to 1.5 mm Hg. The starting material employed was 4,4-difluorohexahydrophthalic anhydride per se. The reaction product was again analyzed by gas chromatographic techniques, and 4-fluorophthalic anhydride was again found to be the major product.

What is claimed is:

1. A process for preparing 4-fluorophthalic anhydride which comprises contacting a dihalohexahydrophthalic anhydride of the formula

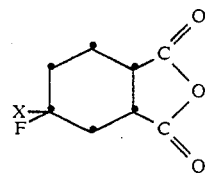

where X is Cl or F with a dehydrogenation catalyst.

2. A process according to claim 1 wherein the dihalohexahydrophthalic anhydride is 4,4-difluorohexahydrophthalic anhydride.

3. A process according to claim 1 wherein the dihalohexahydrophthalic anhydride is 4-chloro-4-fluorohexahydrophthalic anhydride.

4. A process according to claim 2 wherein the catalyst is palladium.

5. A process according to claim 2 wherein the catalyst is platinum.

6. A process according to claim 1 wherein the process is carried out in the liquid phase.

7. A process according to claim 1 wherein the process is carried out in the vapor phase.

8. A process according to claim 1 further comprising conducting said reaction in the presence of a hydrogen acceptor.

9. A process according to claim 8 wherein said hydrogen acceptor is a halocarbon hydrogen acceptor of the formula

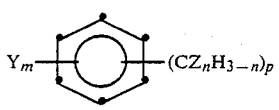

wherein Y is Cl, Br, or I; Z is Cl, Br, or I; m is 0 to 4; n is 0 to 3; p is 0 to 3; and m+n is at least 1; with the proviso that when m is 0, p is at least 1.

10. A process according to claim 8 wherein the dihalohexahydrophthalic anhydride is 4,4-difluorohexahydrophthalic anhydride.

11. A process according to claim 8 wherein the dihalohexahydrophthalic anhydride is 4-chloro-4-fluorohexahydrophthalic anhydride.

12. A process according to claim 10 wherein the hydrogen acceptor is 1,2,4-trichlorobenzene.

13. A process according to claim 10 wherein the hydrogen acceptor is a benzylchloride.

14. A process according to claim 10 wherein the catalyst is palladium.

15. A process according to claim 10 wherein the catalyst is platinum.

16. A process according to claim 10 wherein the reaction is carried out at a temperature between 150° to about 400° C.

17. A process according to claim 10 wherein the process is carried out in the liquid phase.

18. A process according to claim 10 wherein the process is carried out in the vapor phase.

19. A process according to claim 10 wherein the reaction is carried out at a temperature between about 250°–350° C.

20. A process according to claim 10 wherein 4,4-difluorohexahydrophthalic anhydride is contacted with a palladium catalyst in the presence of 1,2,4-trichlorobenzene of a benzylchloride, at a temperature of about 150° to about 400° C.

* * * * *